US011076746B2

(12) United States Patent
Ikeda et al.

(10) Patent No.: US 11,076,746 B2
(45) Date of Patent: Aug. 3, 2021

(54) FLEXIBLE TUBE INSERTION APPARATUS AND FLEXIBLE TUBE INSERTION METHOD

(71) Applicant: OLYMPUS CORPORATION, Tokyo (JP)

(72) Inventors: Yuichi Ikeda, Tama (JP); Takeshi Takahashi, Hachioji (JP); Ryo Tezuka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 174 days.

(21) Appl. No.: 16/448,659

(22) Filed: Jun. 21, 2019

(65) Prior Publication Data
US 2020/0000316 A1  Jan. 2, 2020

Related U.S. Application Data

(63) Continuation of application No. PCT/JP2016/088941, filed on Dec. 27, 2016.

(51) Int. Cl.
*A61B 1/005* (2006.01)
*A61B 1/00* (2006.01)
*A61B 1/31* (2006.01)

(52) U.S. Cl.
CPC .......... *A61B 1/0051* (2013.01); *A61B 1/0005* (2013.01); *A61B 1/00009* (2013.01);
(Continued)

(58) Field of Classification Search
CPC ............ A61B 1/00004; A61B 1/00006; A61B 1/00009; A61B 1/00071; A61B 1/00078;
(Continued)

(56) References Cited

U.S. PATENT DOCUMENTS 4,930,494 A * 6/1990 Takehana ........... A61B 1/00147
600/145
5,060,632 A * 10/1991 Hibino .................. A61B 1/0052
600/109
(Continued)

FOREIGN PATENT DOCUMENTS

JP   H06-304127 A   11/1994
JP   2009-219821 A   10/2009
(Continued)

OTHER PUBLICATIONS

International Search Report dated Feb. 7, 2017 issued in PCT/JP2016/088941.
(Continued)

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

A flexible tube insertion apparatus including a flexible tube to be inserted into an insertion target is provided. The apparatus includes a variable stiffness section disposed in the tube and configured to change a bending stiffness of the tube, a variable stiffness drive section configured to drive the variable stiffness section, a rotation sensor configured to detect rotation of the tube about a central axis, and an insertion shape sensor configured to detect a curved shape of the tube. A variable stiffness controller drives the drive section so that a bending stiffness of the variable stiffness section is increased based on information detected by the rotation sensor and detected by the insertion shape sensor, when the tube forms a loop and rotates about the axis.

6 Claims, 11 Drawing Sheets

(52) U.S. Cl.
CPC ....... *A61B 1/00071* (2013.01); *A61B 1/00158* (2013.01); *A61B 1/31* (2013.01); *G06T 2207/30028* (2013.01)

(58) Field of Classification Search
CPC . A61B 1/00133; A61B 1/00158; A61B 1/005; A61B 1/0051; A61B 1/0055; A61B 1/0056; A61B 1/31; G06T 2207/30028; A61M 25/0054
See application file for complete search history.

(56) References Cited

U.S. PATENT DOCUMENTS

| | | | |
|---|---|---|---|
| 2002/0188174 A1* | 12/2002 | Aizawa | A61B 5/064 600/118 |
| 2005/0228221 A1* | 10/2005 | Hirakawa | A61B 1/00009 600/101 |
| 2006/0135870 A1* | 6/2006 | Webler | A61B 1/00183 600/431 |
| 2007/0038028 A1* | 2/2007 | Uchimura | A61B 1/0055 600/144 |
| 2007/0270649 A1* | 11/2007 | Long | A61B 1/0053 600/144 |
| 2009/0240110 A1* | 9/2009 | Miyawaki | A61B 1/0057 600/149 |
| 2010/0125169 A1* | 5/2010 | Weinberg | G02B 23/2476 600/146 |
| 2011/0196199 A1* | 8/2011 | Donhowe | A61B 1/00147 600/102 |
| 2013/0096423 A1* | 4/2013 | Yamamoto | A61B 1/01 600/424 |
| 2013/0144275 A1* | 6/2013 | Umemoto | A61B 1/0057 606/1 |
| 2019/0231449 A1* | 8/2019 | Diolaiti | A61B 34/20 |

FOREIGN PATENT DOCUMENTS

| | | |
|---|---|---|
| JP | 2011-206332 A | 10/2011 |
| JP | 2013-248346 A | 12/2013 |
| WO | 2016/181484 A1 | 11/2016 |

OTHER PUBLICATIONS

English translation of International Preliminary Report on Patentability dated Jul. 11, 2019, together with the Written Opinion received in related International Application No. PCT/JP2016/088941.

* cited by examiner

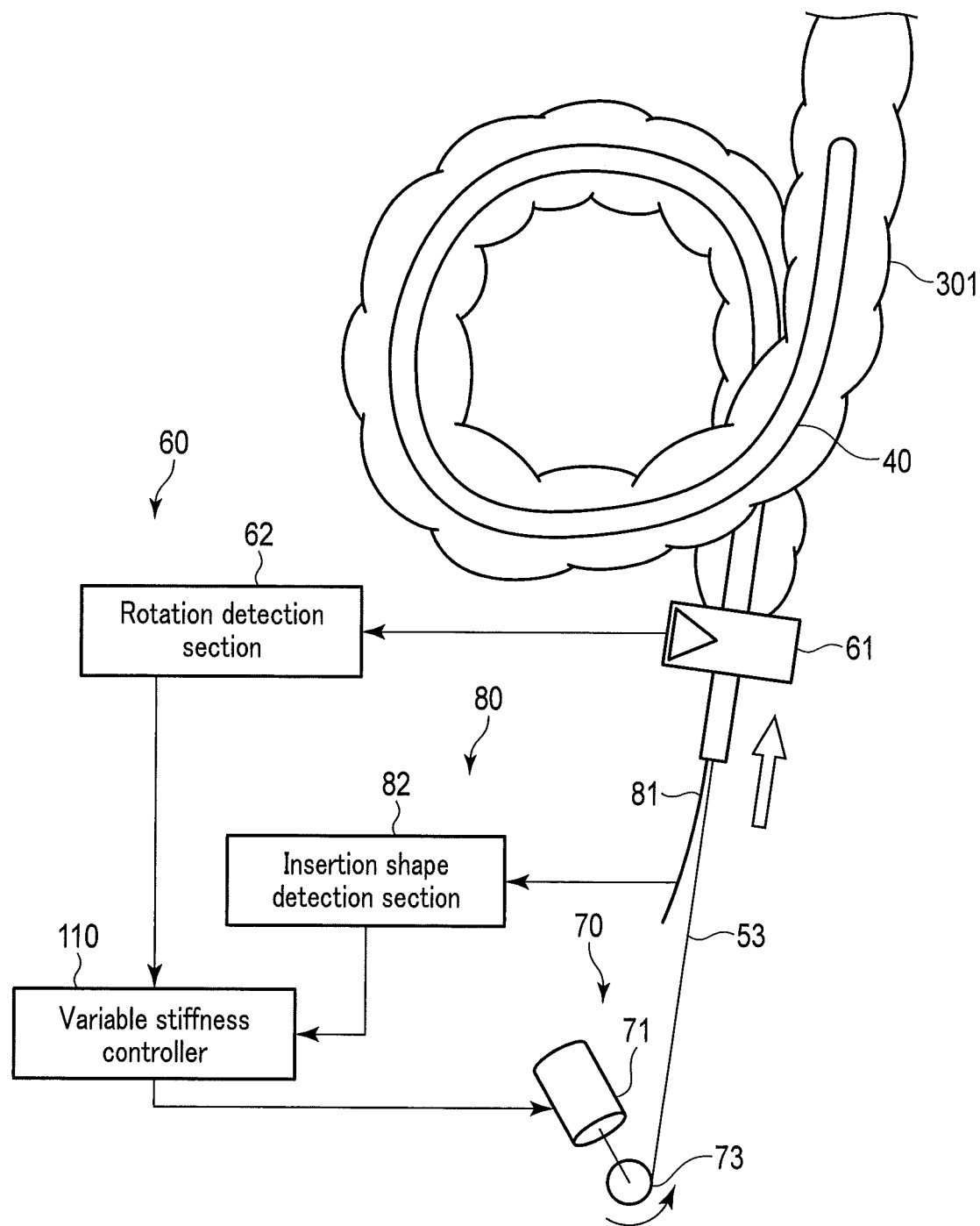
F I G. 3A

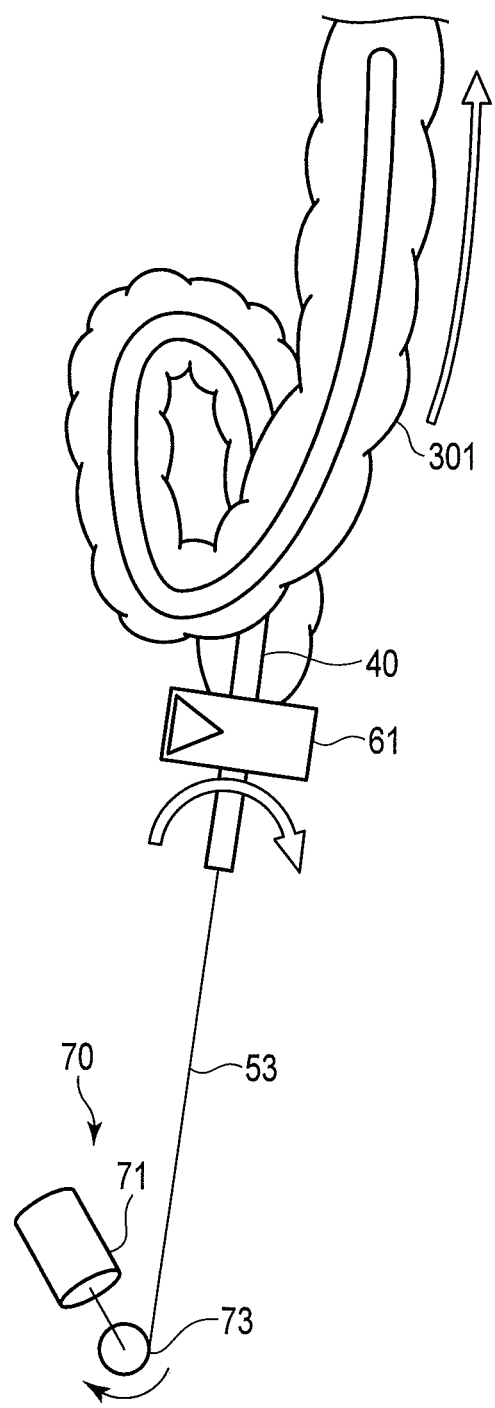
F I G. 3C

FLEXIBLE TUBE INSERTION APPARATUS AND FLEXIBLE TUBE INSERTION METHOD

CROSS-REFERENCE TO RELATED APPLICATIONS

This application is a Continuation Application of PCT Application No. PCT/JP2016/088941, filed Dec. 27, 2016, the entire contents of which are incorporated herein by reference.

BACKGROUND OF THE INVENTION

1. Field of the Invention

The present invention relates to a flexible tube insertion apparatus provided with a flexible tube section to be inserted into an insertion target, and a flexible tube insertion method.

2. Description of the Related Art

For a flexible tube insertion apparatus such as an endoscope apparatus, an insertion operation procedure is known in which when a flexible tube section is inserted into a bent insertion target, such as a large intestine, the insertion target is straightened to facilitate the insertion. For example, in order to straighten the large intestine, the operator performs an operation to push the proximal end side of the flexible tube section into the large intestine so that the tip of the flexible tube is advanced beyond the bent portion of the large intestine. Then, after the advanced flexible tube section forms a loop along the bent shape of the large intestine, the operator turns the loop into a substantially linear shape by an operation of twisting and pulling out the flexible tube section. Thus, the large intestine is straightened.

For the operator to perform an operation to push the flexible tube section, the flexible tube section should desirably have a low bending stiffness so as not to hyperextend the large intestine. On the other hand, for the operator to perform the straightening operation including the operation of twisting and pulling out the flexible tube section, the flexible tube section should desirably have a high bending stiffness in order for the flexible tube section to utilize the linear restoring force.

For example, the endoscope disclosed in Jpn. Pat. Appln. KOKAI Publication No. 2013-248346 has a flexible tube section adapted to easily be passively curved by an external force received from a bent portion of the large intestine at the time of the pushing operation, in order to facilitate the straightening operation. Moreover, in this endoscope, the bending stiffness is increased using the overtube, which covers the flexible tube section during the straightening operation.

BRIEF SUMMARY OF THE INVENTION

An embodiment of the present invention is a flexible tube insertion apparatus. The flexible tube insertion apparatus comprises a flexible tube section that is adapted to be inserted into an insertion target; a variable stiffness section that is disposed in the flexible tube section and configured to change a bending stiffness of the flexible tube section; a variable stiffness drive section configured to drive the variable stiffness section; a rotation detection sensor configured to detect rotation of the flexible tube section about a central axis; an insertion shape detection sensor configured to detect a curved shape of the flexible tube section; and a variable stiffness controller configured to control the variable stiffness drive section so that a bending stiffness of the variable stiffness section is increased based on rotation information detected by the rotation detection sensor and curved shape information detected by the insertion shape detection sensor, when the flexible tube section forms a loop and the flexible tube section rotates about the central axis.

Another embodiment of the present invention is a flexible tube insertion method. The flexible tube insertion method includes: detecting rotation information of a flexible tube section about a central axis, the flexible tube section being adapted to be inserted into an insertion target; detecting curved shape information of the flexible tube section; and controlling a variable stiffness section that is disposed in the flexible tube section and configured to change a bending stiffness of the flexible tube section so that a bending stiffness of the variable stiffness section in response to determining that the flexible tube section forms a loop and the flexible tube section has been rotated about its central axis, based on the detected rotation information and the detected curved shape information.

Advantage of the invention will be set in the description of the follow, and in part will be obvious from the description or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constituent a part of the specification, illustrate embodiments of the invention, and together with the general description given above and the detailed description of the embodiments given below, serve to explain the principles.

FIG. 3A is a diagram showing an example of the operation of the flexible tube insertion apparatus in the embodiment.

FIG. 3C is a diagram showing an example of the operation of the flexible tube insertion apparatus in the embodiment.

DETAILED DESCRIPTION OF THE INVENTION

Hereinafter, the embodiments of the present invention will be described with reference to the drawings.

Figure 1:
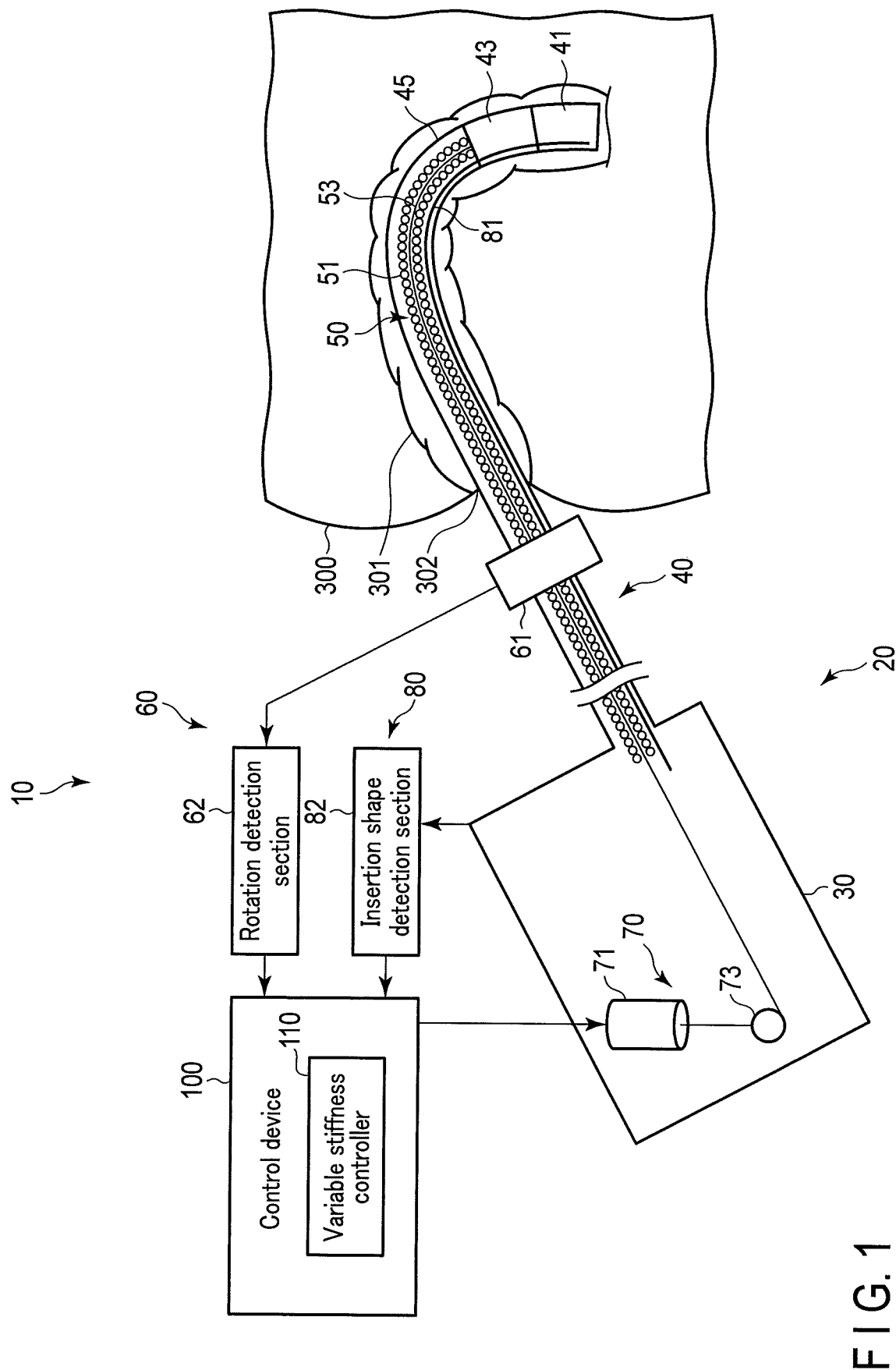
FIG. 1 is a schematic view showing an embodiment of a flexible tube insertion apparatus of the present invention.

FIG. 1 is a schematic view showing an example of a flexible tube insertion apparatus according to an embodiment of the present invention. In the following, the flexible tube insertion apparatus will be described as an endoscope apparatus 10. The endoscope apparatus 10 includes an endoscope 20, a rotation detection sensor 60, an insertion shape detection sensor 80, and a control device 100. The endoscope apparatus 10 includes a light source device, an input device, a display device, and the like (not shown).

The endoscope 20 is, for example, a medical flexible endoscope. In the following, the endoscope 20 will be described as a colonoscope. That is, the description will assume that an insertion target 300 that is the subject of insertion of the endoscope 20 is the large intestine (indicated as an intestine tract 301 in FIG. 1) of a human being. The endoscope 20 may be an industrial flexible endoscope, a catheter, or a treatment tool, and the insertion target 300 may be a lumen, etc. of an animal other than a human being, or other structures.

The endoscope 20 has an insertion section 40 adapted to be inserted into the insertion target, and a control section 30 provided on the proximal end side of the insertion section 40. The insertion section 40 is an elongated tubular section on the endoscope distal end side and has flexibility. The insertion section 40 includes a distal end hard section 41, a bendable section 43, and a soft tube section 45 in the order from the distal end to the proximal end of the insertion section 40. The distal end hard section 41 incorporates an illumination optical system, an observation optical system, an imaging device, and the like (not shown). The bendable section 43 bends in a desired direction when the operator operates the control section 30. The soft tube section 45 is made of fluorine resin or the like and is bendable. Various operations of the endoscope 20 including the bending operation of the bendable section 43 are input to the control section 30.

In addition, since the distal end hard section 41 is only a short section with respect to the entire length of the insertion section 40, the term "flexible tube section" in the present specification is used synonymously with the insertion section 40. That is, the flexible tube section is a section that is adapted to be inserted into the insertion target 300, in the endoscope 20.

The rotation detection sensor 60 includes, for example, an operation section 61 and a rotation detection section 62. The operation section 61 is, for example, a roller attached to the insertion section 40, and is disposed on the proximal end side (hand side) of the soft tube section 45. Part of the soft tube section 45 where the operation section 61 is provided is not inserted in the insertion target 300. The operation section 61 rotates together with the insertion section 40 in accordance with the rotation of the insertion section 40. The rotation detection section 62 is an encoder configured to read a rotational direction of the operation section 61 to detect a rotational movement of the insertion section 40. The rotation detection sensor 60 is installed to detect the rotation of the insertion section 40 about the central axis.

The above-described rotation detection sensor 60 is an example, and the rotation detection sensor 60 is not limited to the type of encoder configured to read the rotation direction of the roller. The rotation detection sensor 60 may be of any type, as long as it functions as a twist detection section configured to detect the twist of the insertion section 40 by the operation section 61 configured to operate in response to the rotation of the insertion section 40 and the rotation detection section 62 configured to detect the rotation of the insertion section 40 in response to the operation of the operation section 61. For example, the rotation detection sensor 60 may have a light-radiating portion configured to emit light toward a scanned section, the scanned section being formed on the surface of the insertion section 40, and a light receiver configured to receive a pattern of the light emitted from the light-radiating portion and reflected by the surface of the insertion section 40 where the scanned section is formed. In this case, the rotation detection sensor 60 functions as a twist detection section of the insertion section 40 by detecting the rotation state of the insertion section 40, based on the difference in the pattern of light received by the light receiver. Other than this, a known detection mechanism configured to detect twist, rotational torque, rotational distortion, and the like around the central axis of the insertion section 40 may be employed as the rotation detection sensor 60.

The insertion shape detection sensor 80 has a detected section 81 disposed in the insertion section 40 and an insertion shape detection section 82. The detected section 81 includes, for example, a source coil array including multiple source coils mutually spaced apart and arranged along the axial direction (longitudinal direction) of the insertion section 40. The insertion shape detection section 82, for example, may include an output section configured to output a voltage applied to each source coil, an output control section configured to control a voltage applied from the output section to each source coil, an antenna configured to receive a magnetic field generated by each source coil, and a shape calculator configured to calculate the curved shape of the insertion section 40 based on the magnetic field received by the antenna. The insertion shape detection sensor 80 is installed to detect the curved shape of the insertion section 40.

The above-mentioned insertion shape detection sensor 80 is an example, and the insertion shape detection sensor 80 is not limited to a magnetic sensor. The insertion shape detection sensor 80 may be any sensor configured to able to detect the curved shape of the insertion section 40, for example, any known detection mechanism such as sensing using electromagnetic waves (electromagnetic sensor), sensing using ultrasonic waves (ultrasonic sensor), sensing using optical loss (optical fiber sensing), sensing using strain (strain sensor), or sensing using an X-ray absorbing material, etc.

The rotation detection section 62 of the rotation detection sensor 60 and the insertion shape detection section 82 of the insertion shape detection sensor 80 are electrically connected to the control device 100. Although the rotation detection section 62 and the insertion shape detection section 82 are separate from the control device 100 in FIG. 1, the rotation detection section 62 and/or the insertion shape detection section 82 may be incorporated in the control device 100.

The control device 100 is connected to the control section 30 of the endoscope 20 through a universal cable (not shown) extending from the control section 30. The control device 100 is also connected to the light source device, the input device, the display device, and the like (not shown). The control device 100 performs various controls of peripheral devices connected thereto such as dimming control of illumination light of the light source device, and stillness/recording of an endoscopic image acquired from the endoscope 20.

The control device 100 comprises a variable stiffness controller 110. The variable stiffness controller 110 is constituted by, for example, a hardware circuit including an ASIC or the like. The variable stiffness controller 110 may be constituted by a processor. When the variable stiffness controller 110 is constituted by a processor, an internal memory or an external memory (not shown) accessible by the processor stores program codes that are executed by the processor for causing the processor to function as the variable stiffness controller 110. The variable stiffness controller 110 controls a hereinafter described variable stiffness drive section 70, based on the rotation of the insertion section 40 detected by the rotation detection section 62 of the rotation detection sensor 60 and the curved shape of the insertion section 40 detected by the insertion shape detection section 82 of the insertion shape detection sensor 80.

A variable stiffness section 50 is provided in the insertion section 40 of the endoscope 20. The variable stiffness section 50 is disposed at least in the soft tube section 45 of the insertion section 40 along the axial direction. The variable stiffness section 50 is disposed, for example, over a predetermined length from the distal end of the soft tube section 45. The variable stiffness section 50 is configured to change the bending stiffness of the insertion section 40 in which the variable stiffness section 50 is disposed, in response to the variable stiffness drive section 70 driven by a drive signal from the variable stiffness controller 110.

The variable stiffness section 50 includes, for example, a coil-like sheath member 51 incorporated in the insertion section 40 and a wire member 53 extending inside the sheath member 51. The sheath member 51 and the wire member 53 are fixed to each other at their tips. The sheath member 51 is configured to expand and contract in the axial direction of the sheath member 51. The reference state of the sheath member 51 is a state in which the sheath member 51 is not expanded or contracted, and the length of the sheath member 51 in the state in which the sheath member 51 is not expanded or contracted is taken as an initial length. The sheath member 51 has, for example, an elastic force that tends to return to the initial length when it is contracted. The proximal end of the wire member 53 is connected to the variable stiffness drive section 70.

The variable stiffness drive section 70 is disposed, for example, in the control section 30. The variable stiffness drive section 70 includes, for example, a motor 71 and a pulley 73 configured to be rotated by a driving force from the motor 71. The wire member 53 is connected to the pulley 73. The motor 71 is driven by a drive signal from the variable stiffness controller 110. The pulley 73 is rotated by the driving force from the motor 71 to pull or loosen the wire member 53. Thus, the variable stiffness drive section 70 drives the variable stiffness section 50.

The change in the bending stiffness of the variable stiffness section 50 will be described.

When it is desired to increase the bending stiffness of the variable stiffness section 50, the variable stiffness controller 110 drives the motor 71 of the variable stiffness drive section 70. Thereby, the pulley 73 pulls the wire member 53 of the variable stiffness section 50. The wire member 53 is pulled toward the proximal end of the insertion section 40. The sheath member 51 is compressed toward the proximal end of the sheath member 51 by the action of pulling the wire member 53. Thereby, the bending stiffness of the sheath member 51 is increased, and the bending stiffness of the insertion section 40, in which the sheath member 51 is disposed, is also increased. For example, when the bending stiffness of the variable stiffness section 50 is low and the insertion section 40 is curved, the insertion section 40 changes from the curved state to the substantially straight state upon increase of the bending stiffness of the variable stiffness section 50 in the above manner.

Conversely, when it is desired to decrease the bending stiffness of the variable stiffness section 50, the variable stiffness controller 110 drives the motor 71 of the variable stiffness drive section 70 in the direction inverse of the direction adopted when increase of the bending stiffness of the variable stiffness section 50 is desired. As a result, the pulley 73 loosens the wire member 53 of the variable stiffness section 50. The wire member 53 is not pulled toward the proximal end of the insertion section 40. Therefore, when the sheath member 51 is compressed toward the proximal end of the sheath member 51 by the action of pulling the wire member 53 as described above, the sheath member 51 is released from the compression towards its proximal end and extends back to its initial length. Thereby, the bending stiffness of the sheath member 51 is reduced, and the bending stiffness of the insertion section 40 in which the sheath member 51 is disposed is also reduced. For example, when the bending stiffness of the variable stiffness section 50 is high and the insertion section 40 is substantially straight, the insertion section 40 changes from the substantially straight state to the state where it is bendable by an external force or the like received from the insertion target 300, upon reduction of the bending stiffness of the variable stiffness section 50 in the above manner.

By driving the motor 71 so as to loosen the wire member 53 from the initial state, the sheath member 51 can extend by more than the initial length, and the bending stiffness of the sheath member 51 as well as the bending stiffness of the insertion section 40, in which the sheath member 51 is disposed, are further reduced. Thereby, the insertion section 40 can be bent more easily.

As such, the bending stiffness of the sheath member 51 changes with the degree to which the wire member 53 is pulled. Therefore, the bending stiffness of the insertion section 40, in which the sheath member 51 is incorporated, also changes depending on the bending stiffness of the sheath member 51. That is, the variable stiffness section 50 changes its own bending stiffness and the bending stiffness of the insertion section 40 in response to the variable stiffness drive section 70, which is driven based on the control signal from the variable stiffness controller 110. The variable stiffness section 50 uniformly changes, for example, the bending stiffness of the entire insertion section 40, in which the variable stiffness section 50 is disposed.

In addition, the pulling amount of the variable stiffness drive section 70 with respect to the wire member 53 is regulated as desired by a regulation mechanism (not shown). The regulation mechanism acts on, for example, at least one of the sheath member 51, the wire member 53, and the variable stiffness drive section 70. Thereby, the highest bending stiffness value and the lowest bending stiffness value of the insertion section 40 are desirably regulated. In an exemplary instance, the highest bending stiffness value is a bending stiffness value at which the insertion section 40 is substantially straightened, and does not include the bending stiffness value in a state where the insertion section 40 is bent due to excessive pulling of the wire member 53.

The variable stiffness section 50 may include variable stiffness units. That is, the variable stiffness section 50 can include, for example, variable stiffness units each including the own sheath member 51 and wire member 53. Each of the variable stiffness units has the own variable stiffness drive section 70, and can be controlled independently of each other by a control signal from the variable stiffness controller 110.

Next, the operation of the endoscope apparatus 10 will be described.

The insertion section 40 of the endoscope 20 is inserted from the anus 302 into the intestine tract 301 by the operator. The insertion section 40 advances in the intestine tract 301 while curving in a manner that follows the shape of the intestine tract 301. The endoscope 20 converts light from a subject in the intestine tract 301 into an electrical signal through the imaging device (not shown) incorporated in the distal end hard section 41. Then, the electrical signal is transmitted to the control device 100. The control device 100 acquires the electrical signal and converts the acquired electrical signal into a video signal. The control device 100 causes the display device (not shown) to display an endoscopic observation image based on the video signal.

In the insertion shape detection sensor 80 during insertion, the output control section of the insertion shape detection section 82 applies a voltage from the output section to the detected section 81 as the source coils. As a result, the detected section 81 generates a weak magnetic field around the detected section 81. The antenna of the insertion shape detection section 82 detects the magnetic field generated by the detected section 81. Then, the shape calculator of the insertion shape detection section 82 calculates the curved shape of the insertion section 40 based on the magnetic field detected by the antenna. The information on the calculated curved shape of the insertion section 40 is transmitted from the insertion shape detection section 82 to the variable stiffness controller 110. Further, the calculated curved shape of the insertion section 40 is displayed as a computer graphics image on the display device (not shown) through the control device 100.

In addition, when the insertion section 40 rotates (twists) during insertion, the operation section 61 of the rotation detection sensor 60 rotates with the insertion section 40. The rotation detection section 62 reads the rotation direction of the operation section 61 rotated together with the insertion section 40 to detect the rotation state of the insertion section 40. The detected rotation information of the insertion section 40 is transmitted from the rotation detection section 62 to the variable stiffness controller 110.

The variable stiffness controller 110 acquires the rotation information detected by the rotation detection sensor 60 and the curved shape information detected by the insertion shape detection sensor 80. Then, the variable stiffness controller 110 sends a drive signal for driving the variable stiffness drive section 70 to the variable stiffness drive section 70 in order to change the bending stiffness of the variable stiffness section 50 based on the acquired information set. Thereby, the variable stiffness drive section 70 is driven, so that the bending stiffness of the variable stiffness section 50 is changed.

As described above, in the endoscope apparatus 10, the variable stiffness controller 110 can drive the variable stiffness drive section 70 to change the bending stiffness of the variable stiffness section 50 according to the rotational state and curved state of the insertion section 40 at the time of insertion, so that the bending stiffness of the insertion section 40 can be changed.

Next, the straightening operation for the insertion target 300 at the time of insertion in the embodiment of the present invention will be described with reference to FIGS. 2A to 2D.

In the following description, a deep section indicates a position ahead of the current position in the insertion direction of the insertion section 40. The pushing operation of the insertion section 40 refers to an operation of pushing the insertion section 40 into the intestine tract 301 in a state where the distal end of the insertion section 40 is inserted into the intestine tract 301, by applying a pressing force from the side of the hand holding the insertion section 40 toward the distal end side of the insertion section 40. By the pushing operation, the distal end of the insertion section 40 moves forward in the intestine tract 301 toward the deep section. The pull-out operation of the insertion section 40 refers to an operation of pulling out the insertion section 40 from the inside of the intestine tract 301 in a state where the distal end of the insertion section 40 is inserted into the intestine tract 301, by applying a pull-out force from the side of the hand holding the insertion section 40 toward the proximal end side of the insertion section 40. Through the pull-out operation, the distal end of the insertion section 40 moves backward toward the anus 302, which is the entrance of the intestine tract 301.

Figure 2A:
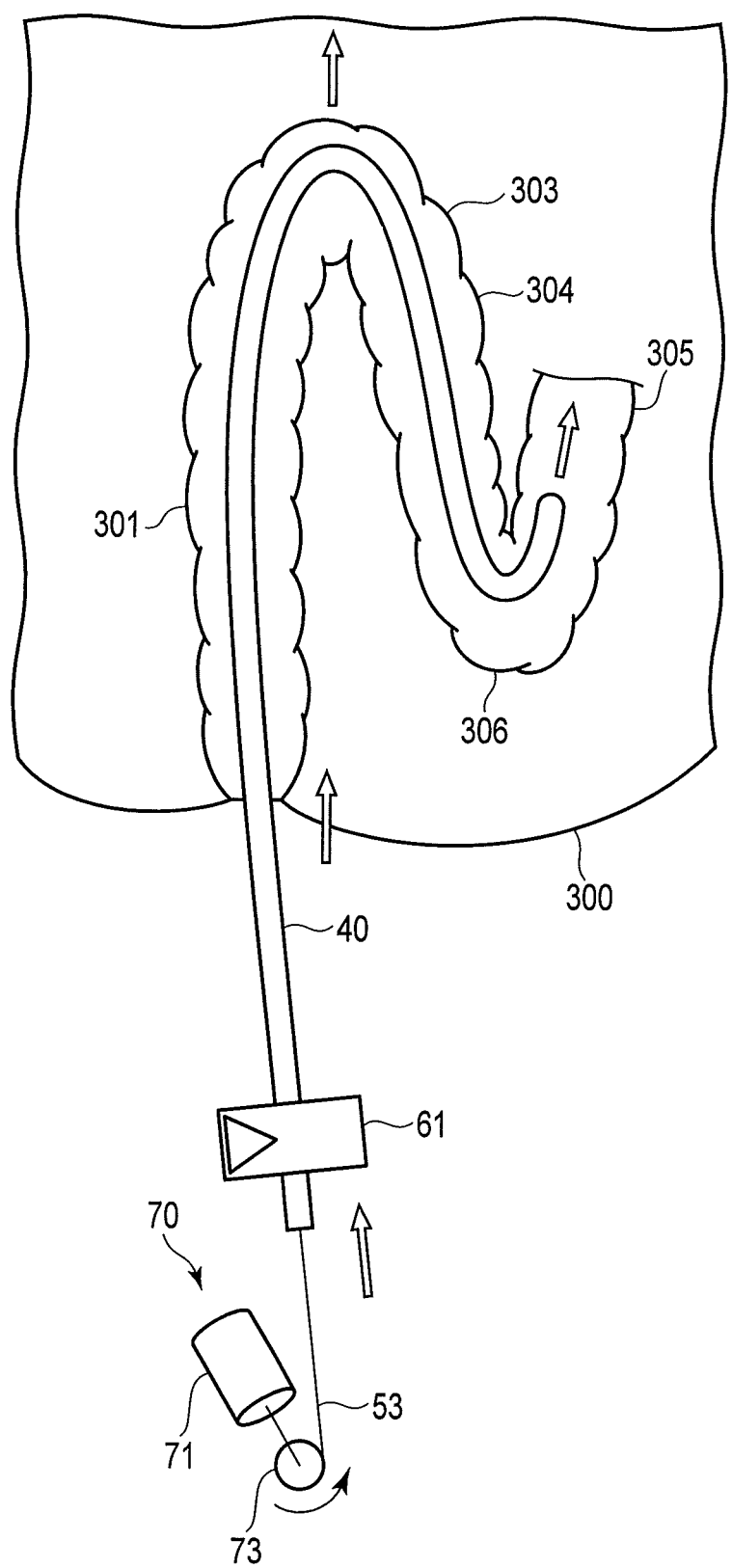
FIG. 2A is a diagram showing an example of the operation of the flexible tube insertion apparatus in the embodiment.

The operator inserts the insertion section 40 of the endoscope 20 from the anus 302 in a state where the bending stiffness value of the variable stiffness section 50 is low, and then performs the pushing operation. The state in which the bending stiffness value of the variable stiffness section 50 is low means, for example, a state in which the sheath member 51 of the variable stiffness section 50 is in the reference state. As shown in FIG. 2A, the insertion section 40 is inserted into the sigmoid colon-descending colon curve (S-D bent section) 306, which is the bent portion between the sigmoid colon 303 and the descending colon 305, in an N shape (referred to herein as an N-loop, although not strictly a loop), in a state in which the sigmoid colon 303 and the intestinal membrane 304 are hyperextended. At the time of the pushing operation, in order to suppress hyperextension of the intestine tract 301 as much as possible, and to allow the insertion section 40 to easily pass the bent portion 306, the variable stiffness controller 110 controls the variable stiffness drive section 70 so that the bending stiffness value of the variable stiffness section 50 is decreased (loosened) when the pushing operation is detected by a forward/backward sensor such as the rotation detection sensor 60 or the insertion shape detection sensor 80. When the bending stiffness value of the variable stiffness section 50 is low, the bending stiffness of the insertion section 40 is also low, so the insertion section 40 moves forward toward the deep section along the curve of the intestine tract 301 without applying a load to the intestine tract 301 due to the pushing operation.

Figure 2B:
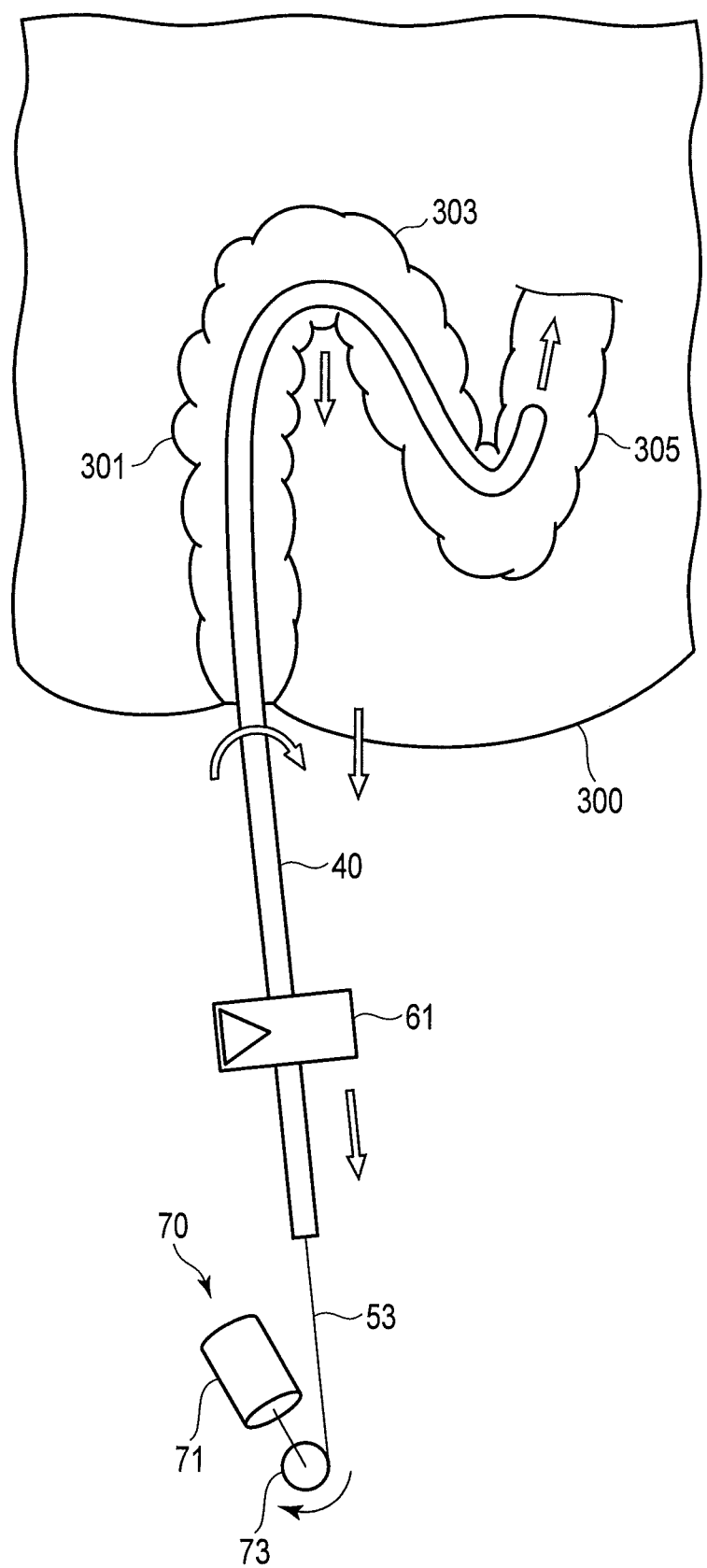
FIG. 2B is a diagram showing an example of the operation of the flexible tube insertion apparatus in the embodiment.

Subsequently, as shown in FIG. 2B, the operator performs the pull-out operation and slowly applies a right rotation to the insertion section 40. As a result, the angle between the sigmoid colon 303 and the descending colon 305 is increased, so that the sigmoid colon 303 has a substantially sine curve. In order to promote the straightening of the intestine tract 301, the variable stiffness controller 110 controls the variable stiffness drive section 70 so that the bending stiffness value of the variable stiffness section 50 is increased when the pull-out operation is detected by the forward/backward sensor, such as the rotation detection sensor 60 or the insertion shape detection sensor 80. When the bending stiffness value of the variable stiffness section 50 is high, since the bending stiffness of the insertion section 40 is also high, the insertion section 40 is urged so that its curvature radius is increased.

Figure 2C:
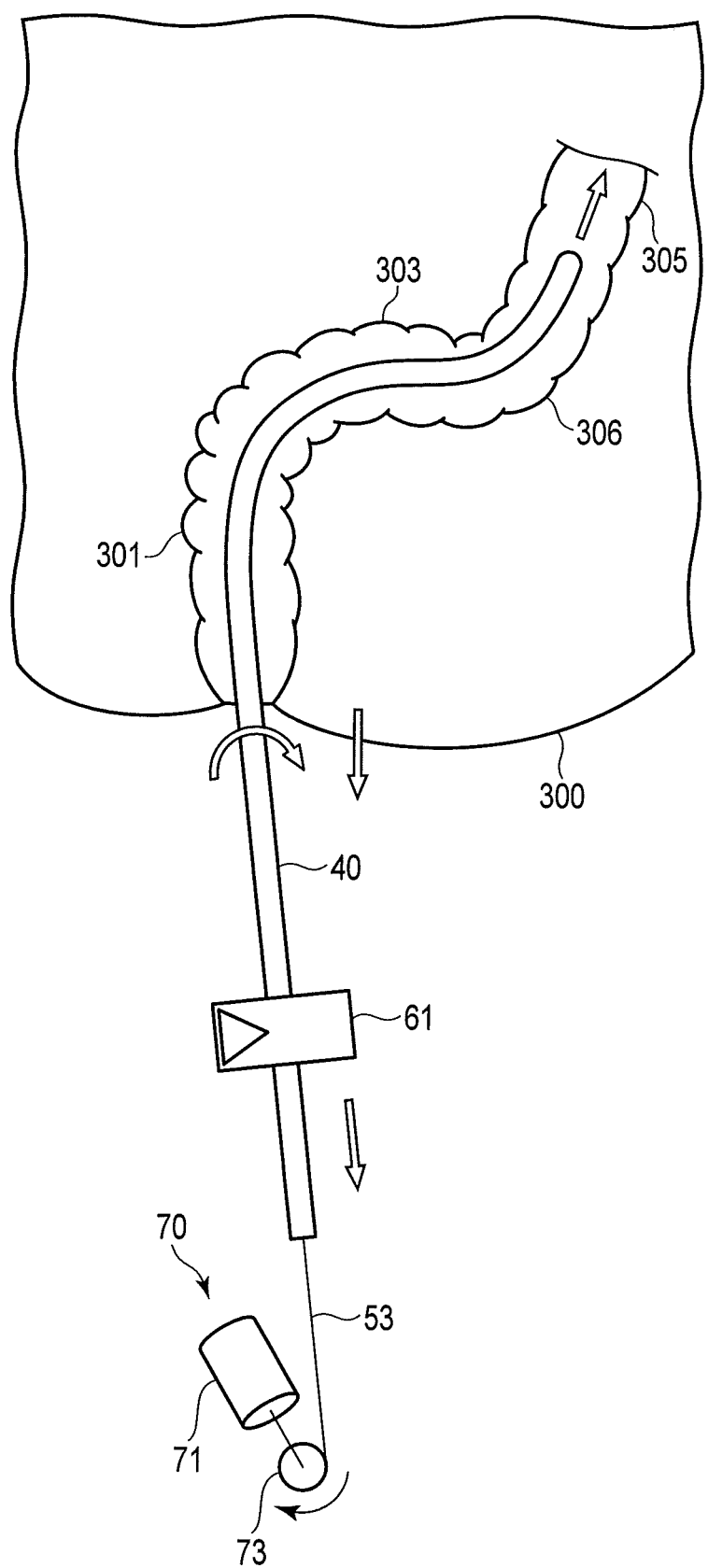
FIG. 2C is a diagram showing an example of the operation of the flexible tube insertion apparatus in the embodiment.

As the operator continues the above-described pull-out operation and right rotation, the angle formed by the sigmoid colon 303 and the descending colon 305 is more widely opened and straightened as shown in FIG. 2C. That is, the S-D bent portion 306 gradually deforms into linear due to the high bending stiffness of the insertion section 40.

Figure 2D:
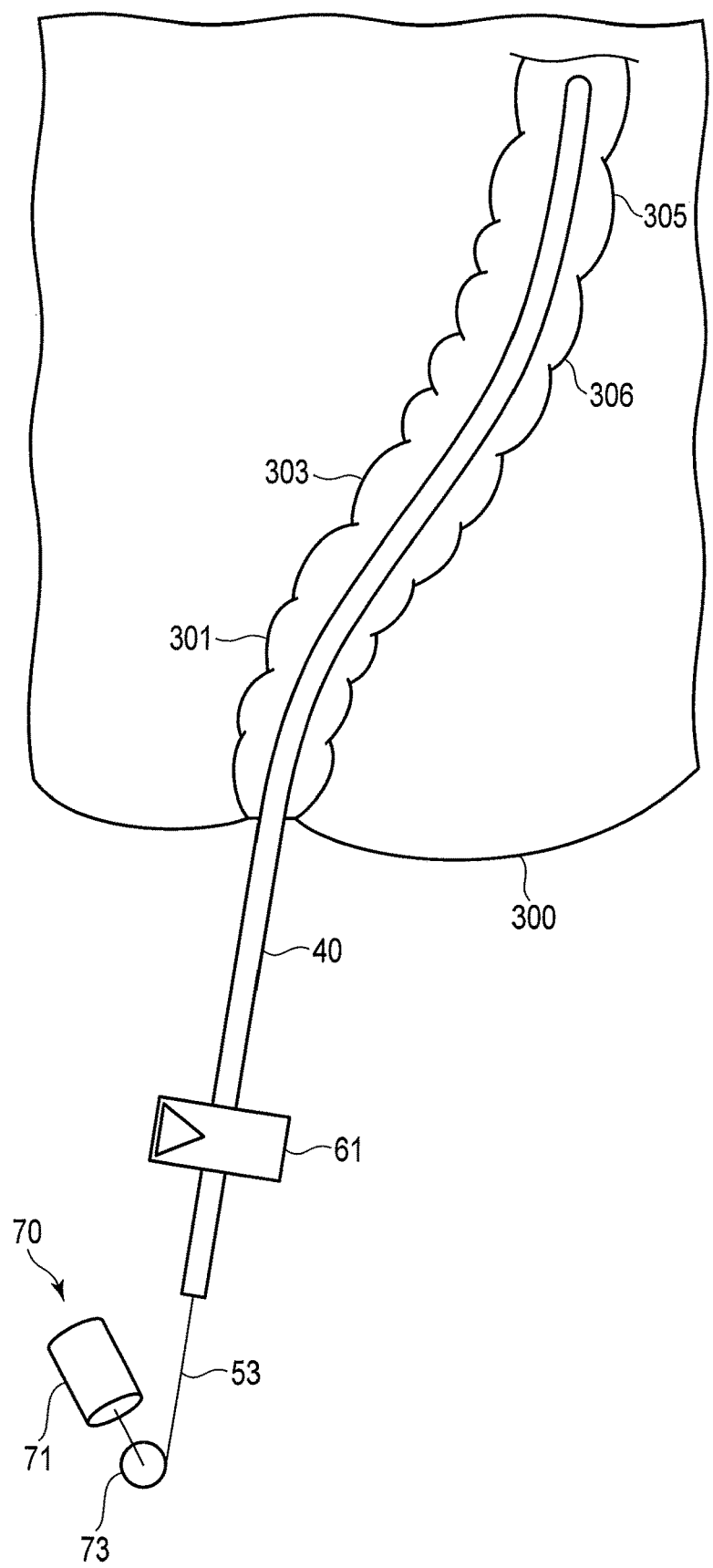
FIG. 2D is a diagram showing an example of the operation of the flexible tube insertion apparatus in the embodiment.

As shown in FIG. 2D, when the sigmoid colon 303 is straightened, the insertion section 40 can be easily inserted to the deep section. Therefore, the variable stiffness controller 110 controls the variable stiffness drive section 70 so that the bending stiffness value of the variable stiffness section 50 is decreased, in response to detecting that the sigmoid colon 303 has been straightened, that is, the insertion section 40 has been straightened, based on the curved shape of the insertion section 40 detected by the insertion shape detection sensor 80. Thereafter, the insertion section 40 is advanced to a deeper position by the pushing operation. The variable stiffness controller 110 stops the variable stiffness drive section 70 when it detects that the movement operation of the insertion section 40 is stopped by the movement sensor, such as the rotation detection sensor 60 or the insertion shape detection sensor 80.

The endoscope 20 can be easily inserted into the deep section of the insertion target by the straightening operation accompanied by the N loop-release of the insertion target, as described with reference to FIGS. 2A to 2D.

Next, the straightening operation for the insertion target in the case where the insertion section 40 forms a loop as the insertion proceeds will be described with reference to FIGS. 3A to 3D.

When the insertion section 40 forms, for example, an α-shaped loop (α-loop), since it is difficult for the operator's force, when pushing the insertion section 40 from the proximal side, to be transmitted to the tip of the insertion section 40, insertion to the deep section will be difficult. When the loop is formed to a certain extent, the loop releasing and straightening operations are performed by combining the pushing operation and the subsequent pull-out operation with the rotational operation in a manner similar to the above-described straightening operation. In the present embodiment, the rotation detection sensor 60 and the insertion shape detection sensor 80 detect the rotation operation and the loop shape of the insertion section 40, and then the variable stiffness controller 110 changes the bending stiffness of the variable stiffness section 50 based on the detection, thereby assisting the loop releasing and straightening operations and helping to insert the insertion section 40 to the deep section.

The operator inserts the insertion section 40 of the endoscope 20 from the anus 302 in a state where the bending stiffness value of the variable stiffness section 50 is low, and then performs the pushing operation. For example, as shown in FIG. 3A, the distal end of the insertion section 40 advances along the bent shape of the intestine tract 301 toward the deep section while forming a left-handed loop (counterclockwise loop), in which the distal end side of the insertion section 40 is above and overlaps the proximal end side of the insertion section 40. During the insertion, the insertion shape detection sensor 80 detects the curved shape of the insertion section 40 to transmit the detection result to the variable stiffness controller 110 of the control device 100.

When the insertion section 40 forms a loop, since the pushing operation is hard to be transmitted to the distal end of the insertion section 40, insertion to the deep section will be difficult. For this reason, in order to insert the insertion section 40 to the deep section, it is necessary to release the loop of the insertion section 40 and straighten the insertion target. Thus, the operator initiates the loop releasing and straightening operations in such situations.

Figure 3B:
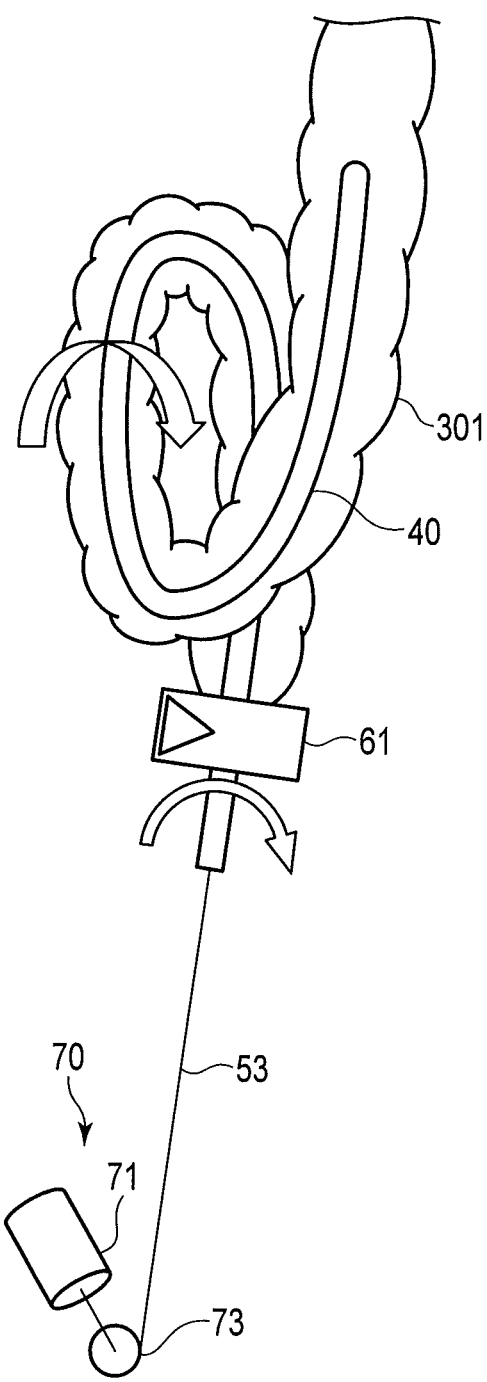
FIG. 3B is a diagram showing an example of the operation of the flexible tube insertion apparatus in the embodiment.

As shown in FIG. 3B, the operator slowly applies a right turn to the insertion section 40 in order to release the loop of the insertion section 40. That is, the insertion section 40 is slowly twisted to the right from the hand side of the insertion section 40. The rotation detection sensor 60 detects that the insertion section 40 is turned to the right to transmit the detection result to the variable stiffness controller 110 of the control device 100.

The variable stiffness controller 110 is informed that the insertion shape detection sensor 80 has detected that the insertion section 40 forms a loop in which the distal end side is above and overlaps the proximal end side, and the rotation detection sensor 60 has detected that the insertion section 40 is turned to the right. Based on the information detected by the rotation detection sensor 60 and the insertion shape detection sensor 80, the variable stiffness controller 110 determines that the loop releasing operation of the insertion section 40 for the purpose of straightening the insertion target has started.

In order to proceed with the loop releasing and straightening operations, it is desirable that the bending stiffness of the insertion section 40 be high, as described in relation to the straightening operation with reference to FIGS. 2B and 2C. Therefore, the variable stiffness controller 110 instructs the variable stiffness drive section 70 to increase the bending stiffness value of the variable stiffness section 50. For example, as shown in FIG. 3C, in a state where the operator twists the hand side of the insertion section 40 to the right, the motor 71 of the variable stiffness drive section 70 is driven, so that the wire member 53 is pulled to the proximal end side of the insertion section 40 by the driving force. Thereby, the bending stiffness value of the variable stiffness section 50 becomes large, so that the bending stiffness of the insertion section 40 increases. In addition to the loop-releasing force from the right twist applied by the operator, the insertion section 40 exerts a restoring force to restore the straight state due to the increase of the bending stiffness. By the restoring force, the insertion section 40 is gradually loop-released and straightened. At the time of loop releasing and straightening, the operator performs the pull-out operation as appropriate, in addition to the right rotation operation of the insertion section 40 as described with reference to FIGS. 2B and 2C.

Figure 3D:
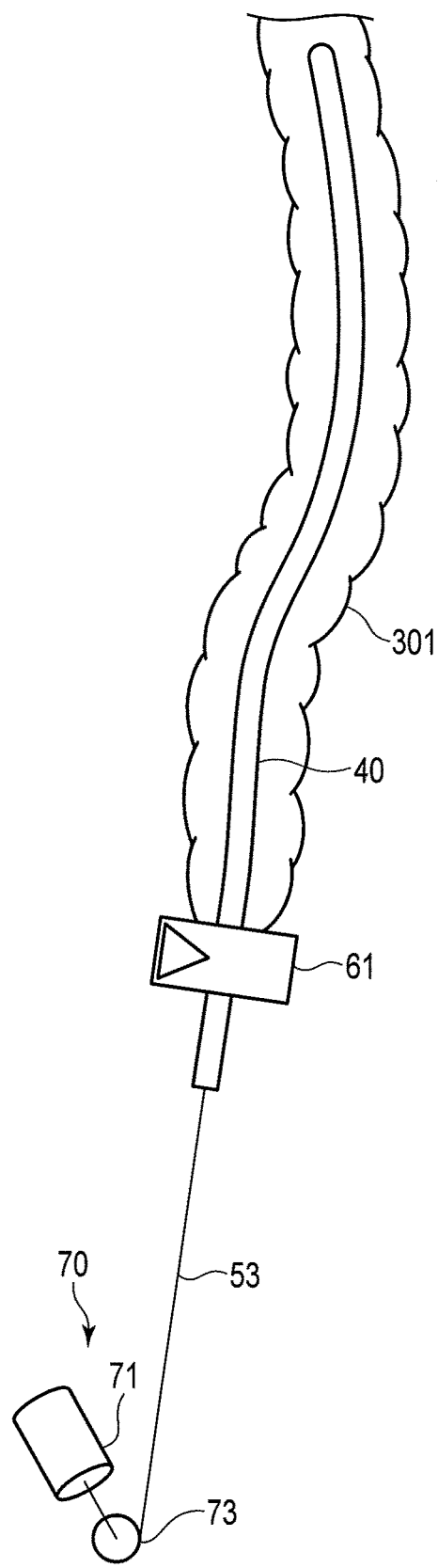
FIG. 3D is a diagram showing an example of the operation of the flexible tube insertion apparatus in the embodiment.

As shown in FIG. 3D, the loop releasing and straightening operations are completed. Thereby, the insertion section 40 can be easily inserted into the deep section. Therefore, the variable stiffness controller 110 controls the variable stiffness drive section 70 so that the bending stiffness value of the variable stiffness section 50 is decreased, in response to detecting that the loop has been released; that is, the insertion section 40 has been straightened, based on the curved shape of the insertion section 40 detected by the insertion shape detection sensor 80. Thereafter, the insertion section 40 is advanced to a deeper position by the pushing operation.

As such, the endoscope apparatus 10 that allows the loop releasing and straightening operations of the insertion section 40 to be easily performed is provided by the bending stiffness control by the variable stiffness controller 110 as described above.

Figure 4:
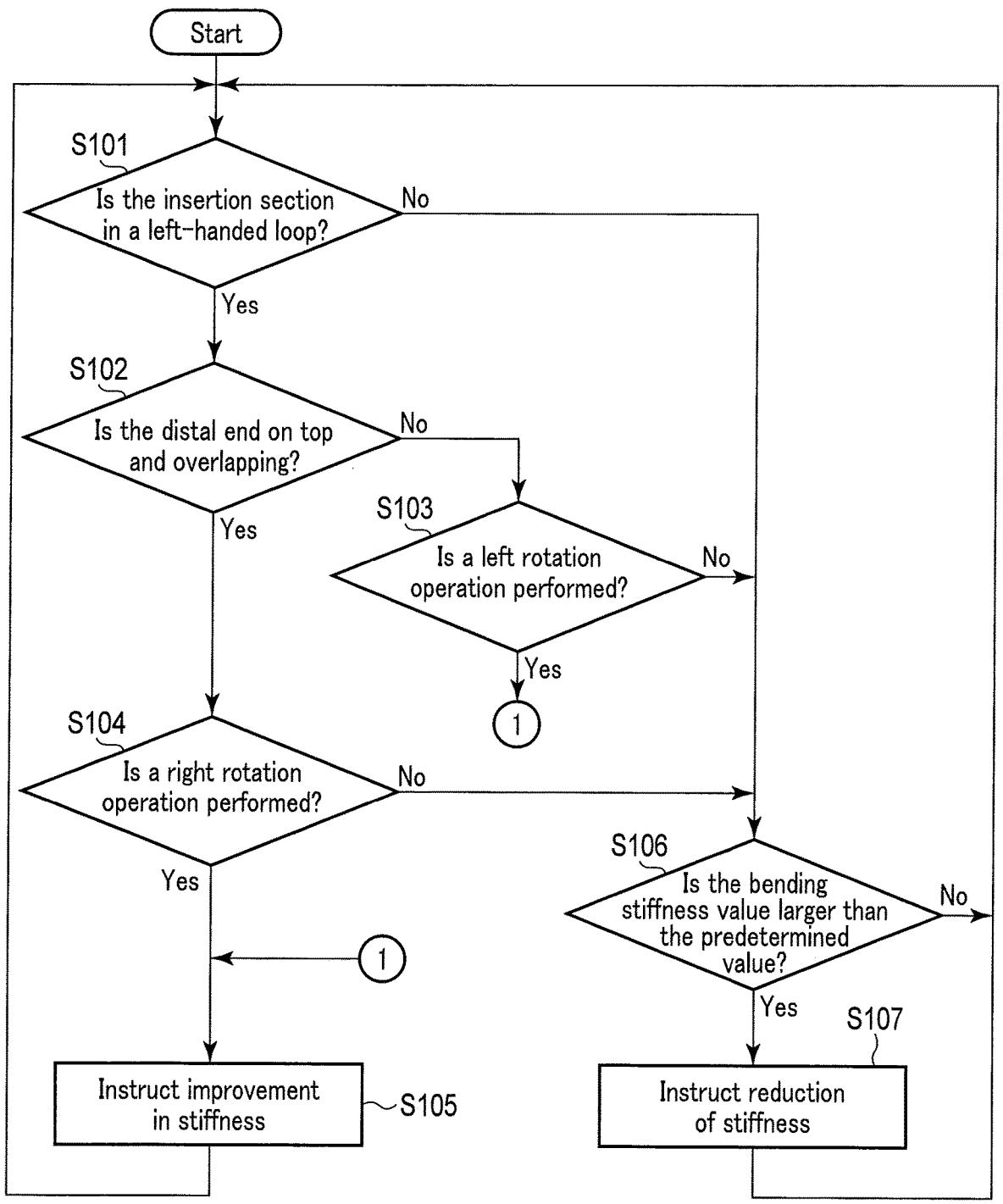
FIG. 4 is a flowchart showing an example of the operation of the flexible tube insertion apparatus in the embodiment.

FIG. 4 is a flowchart showing an example of the stiffness variable control by the control device 100 for the loop releasing and straightening operations in the present embodiment.

In step S101, the variable stiffness controller 110 of the control device 100 determines whether or not the insertion section 40 forms a left-handed loop based on the curved shape of the insertion section 40 detected by the insertion shape detection sensor 80. If the variable stiffness controller 110 determines that the insertion section 40 does not form a left-handed loop (No), the process proceeds to step S106. On the other hand, if the variable stiffness controller 110 determines that the insertion section 40 forms a left-handed loop (Yes), the process proceeds to step S102.

In step S102, the variable stiffness controller 110 determines whether or not the distal end side of the insertion section 40 is above and overlaps the proximal end side of the insertion section 40 based on the curved shape of the insertion section 40 detected by the insertion shape detection sensor 80. If the variable stiffness controller 110 determines that the distal end side of the insertion section 40 is not above and overlaps the proximal end side of the insertion section 40 (No), the process proceeds to step S103. On the other hand, if the variable stiffness controller 110 determines that the distal end side of the insertion section 40 is above and overlaps the proximal end side of the insertion section 40 (Yes), the process proceeds to step S104.

In step S103, the variable stiffness controller 110 determines whether or not the left rotation operation of the insertion section 40 is performed based on the rotation of the insertion section 40 detected by the rotation detection sensor 60. If the variable stiffness controller 110 determines that the left rotation operation of the insertion section 40 is performed (Yes), the process proceeds to step S105. On the other hand, if the variable stiffness controller 110 determines that the left rotation operation of the insertion section 40 is not performed (No), the process proceeds to step S106.

In step S104, the variable stiffness controller 110 determines whether or not the right rotation operation of the insertion section 40 is performed based on the rotation of the insertion section 40 detected by the rotation detection sensor 60. If the variable stiffness controller 110 determines that the right rotation operation of the insertion section 40 is performed (Yes), the process proceeds to step S105. On the other hand, if the variable stiffness controller 110 determines that the right rotation operation of the insertion section 40 is not performed (No), the process proceeds to step S106.

Figure 5A:
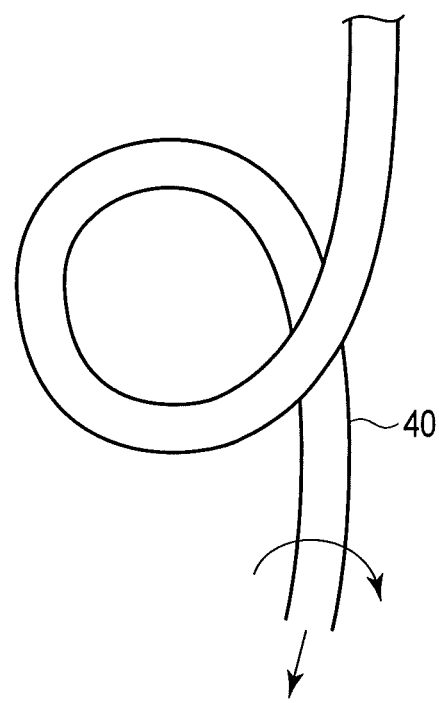
FIG. 5A is a diagram showing a left-handed loop in which the distal end side of an insertion section is above and overlaps the proximal end side of the insertion section.
Figure 5B:
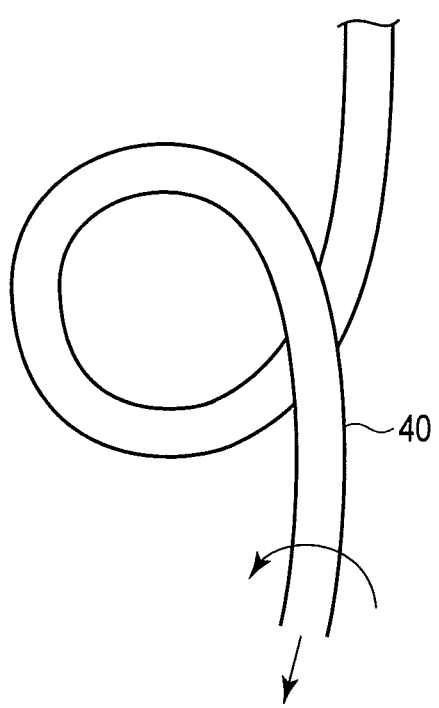
FIG. 5B is a diagram showing a left-handed loop in which the proximal end side of the insertion section is above and overlaps the distal end side of the insertion section.

If the process proceeds to YES in step S103 or S104, the process proceeds to step S105. That is, in the case where the insertion section 40 forms a left-handed loop, the distal end side of the insertion section 40 is not above with overlapping, and the left rotation operation of the insertion section 40 is performed as shown in FIG. 5B (step S103—Yes), and in the case where the insertion section 40 forms a left-handed loop, and the distal end side of the insertion sections 40 is above with overlapping, and the right rotation operation of the insertion section 40 is performed as shown in FIG. 5A (Step S104—Yes), the process proceeds to step S105. At this time, the variable stiffness controller 110 determines that the operator performs the loop releasing operation of the insertion section 40 for the purpose of straightening the insertion target 300. For example, through the right rotation operation and the pull-out operation shown in FIG. 5A, the loop of the insertion section 40 is rotated clockwise toward the upper side of the drawing and released accordingly. Further, through the left-handed rotation operation and the pull-out operation shown in FIG. 5B, the loop of the insertion section 40 is rotated counterclockwise toward the lower side of the drawing, and released accordingly.

In step S105, the variable stiffness controller 110 drives the variable stiffness drive section 70 so that the bending stiffness value of the variable stiffness section 50 is increased. For example, the variable stiffness controller 110 sends a drive signal to the variable stiffness drive section 70 to drive the motor 71 of the variable stiffness drive section 70. Thereby, the wire member 53 of the variable stiffness section 50 is pulled to compress the sheath member 51, so that the bending stiffness of the insertion section 40 is increased.

By increasing the bending stiffness of the insertion section 40 forming the loop, the force to restore the loop shape of the insertion section 40 to the linear shape is increased. The restoring force assists in the loop releasing and straightening operations of the insertion section 40 shown in FIGS. 5A and 5B. That is, since increasing the bending stiffness of the insertion section 40 during the rotation operation and the pull-out operation performed by the operator when the insertion section 40 forms a loop increases the tendency that the insertion section 40 restores its linear shape, the loop releasing and straightening operations of the insertion section 40 is assisted.

After step S105, the process returns to step S101. And the process is repeated from step S101.

When No is selected in step S101, S103, or S104, the process proceeds to step S106. That is, in the case where the insertion section 40 does not form a left-handed loop (step S101—No), in the case where the insertion section 40 forms a left-handed loop, the distal end side of the insertion section 40 is not above and overlaps the proximal end side of the insertion section 40, and the left rotation operation of the insertion section 40 is not performed (step S103—No), or in the case where the insertion section 40 forms a left-handed loop, the distal end side of the insertion section 40 is above and overlaps the proximal end side of the insertion section 40, and the right rotation operation of the insertion section 40 is not performed (step S104—No), the variable stiffness controller 110 determines whether or not the bending stiffness value of the variable stiffness section 50 is larger than a predetermined value in step S106. The variable stiffness controller 110, for example, obtains information concerning the bending stiffness value of the variable stiffness section 50 from the information on the state of the pulley 73 of the variable stiffness drive section 70 to determine whether or not the bending stiffness value of the variable stiffness section 50 is greater than a predetermined value. The predetermined value can be appropriately set within the range that the bending stiffness value of the variable stiffness section 50 can take, and is, for example, the bending stiffness value when the sheath member 51 of the variable stiffness section 50 is in the reference state.

In step S106, if the variable stiffness controller 110 determines that the bending stiffness value of the variable stiffness section 50 is larger than the predetermined value (Yes), the process proceeds to step S107. Then, the variable stiffness controller 110 drives the variable stiffness drive section 70 so that the bending stiffness value of the variable stiffness section 50 is decreased. For example, the variable stiffness controller 110 sends the drive signal to the variable stiffness drive section 70 to drive the motor 71 of the variable stiffness drive section 70. As a result, the pulley 73 of the variable stiffness drive section 70 is loosened to cause the sheath member 51 of the variable stiffness section 50 to be extended, so that the bending stiffness of the insertion section 40 is reduced.

After step S107, the process returns to step S101. And the process is repeated from step S101.

On the other hand, in step S106, if the variable stiffness controller 110 determines that the bending stiffness value of the variable stiffness section 50 is equal to or less than the predetermined value (No), the process returns to step S101. That is, if the bending stiffness value of the variable stiffness section 50 is equal to or less than the predetermined value, the variable stiffness controller 110 does not change the bending stiffness value of the variable stiffness section 50. The process is repeated from step S101.

Thus, when the loop of the insertion section 40 is not formed, the variable stiffness controller 110 proceeds the processes with the cycle of step S101, step S106, and step S101. The bending stiffness value of the variable stiffness section 50 maintains the bending stiffness value of the sheath member 51 in the reference state, for example.

In addition, even if the loop of the insertion section 40 is formed, if the operator does not twist the hand side of the insertion section 40, the variable stiffness controller 110 proceeds the processes with the cycle of step S101, step S102, step S103/step S104, step S106, and step S101. The bending stiffness value of the variable stiffness section 50 maintains the bending stiffness value of the sheath member 51 in the reference state, for example.

When a loop of the insertion section 40 is formed and the operator twists the hand side of the insertion section 40, the variable stiffness controller 110 proceeds the processes with the cycle of step S101, step S102, step S103/step S104, step S105, and step S101. The bending stiffness value of the variable stiffness section 50 gradually increases as this cycle is repeated. Thereby, the loop releasing and straightening operations is assisted.

When the loop of the insertion section 40 is released, the variable stiffness controller 110 proceeds the processes with the cycle of step S101, step S106, and step S107. The bending stiffness value of the variable stiffness section 50 gradually decreases as this cycle is repeated.

When the operator stops the twist on the hand side of the insertion section 40 when the loop is formed in the insertion section 40, the variable stiffness controller 110 proceeds the processes with the cycle of step S101, step S102, step S103/step S104, step S106, and step S107, and accordingly the bending stiffness value of the variable stiffness section 50 gradually decreases. In this case, by additionally using the detection of the pull-out operation or the pushing operation of the insertion section 40 by the forward/backward sensor, such as the rotation detection sensor 60 and the insertion shape detection sensor 80, the variable stiffness controller 110 may appropriately control the bending stiffness of the variable stiffness section 50.

As described above, in the present embodiment, the variable stiffness controller 110 controls the variable stiffness drive section 70 so that the bending stiffness of the insertion section 40 is increased based on the information detected by the rotation detection sensor 60 and the information detected by the insertion shape detection sensor 80, when the insertion section 40 forms a loop (for example, the N-loop shown in FIG. 2A or the α-loop shown in FIG. 3A) and the insertion section 40 is rotated. The rotation operation performed when the insertion section 40 forms a loop is the operation by the operator to release the loop and straighten the insertion target. Thus, increasing the bending stiffness of the insertion section 40 during this operation allows the insertion section 40 itself to be easily restored to a linear shape. This assists the loop releasing and straightening of the insertion section 40.

Further, in the present embodiment, the variable stiffness controller 110 controls the variable stiffness drive section 70 so that the bending stiffness of the insertion section 40 is increased based on the information detected by the rotation detection sensor 60 and the information detected by the insertion shape detection sensor 80, when the insertion section 40 forms a loop with a crossover (e.g., the α-loop shown in FIG. 3A), the loop is left-handed from the hand side to the distal side of the insertion section 40, the hand side of the insertion section 40 crosses the distal side of the insertion section 40 so as to be below the distal side of the insertion section 40, and the insertion section 40 is being subjected to right rotation. Further, the variable stiffness controller 110 controls the variable stiffness drive section 70 so that the bending stiffness of the insertion section 40 is increased based on the information detected by the rotation detection sensor 60 and the information detected by the insertion shape detection sensor 80, when the insertion section 40 forms a loop with a crossover, the loop is left-handed from the hand side to the distal side of the insertion section 40, the hand side of the insertion section 40 crosses the distal side of the insertion section 40 so as to be above the distal side of the insertion section 40, and the insertion section 40 is being subjected to left rotation. Such control can also assist the loop releasing and straightening of the insertion section 40.

For example, the variable stiffness controller 110 controls the variable stiffness drive section 70 so that the bending stiffness of the insertion section 40 is increased based on the information detected by the rotation detection sensor 60 and the information detected by the insertion shape detection sensor 80, based on the same principle as described above, even when the insertion section 40 forms a loop with a crossover, the loop is right-handed from the hand side to the distal side of the insertion section 40, the hand side of the insertion section 40 crosses the distal side of the insertion section 40 so as to be below the distal side of the insertion section 40, and the insertion section 40 is being subjected to left rotation. In addition, the variable stiffness controller 110 controls the variable stiffness drive section 70 so that the bending stiffness of the insertion section 40 is increased based on the information detected by the rotation detection sensor 60 and the information detected by the insertion shape detection sensor 80, based on the same principle as described above, even when the insertion section 40 forms a loop with a crossover, the loop is right-handed from the hand side to the distal side of the insertion section 40, the hand side of the insertion section 40 crosses the distal side of the insertion section 40 so as to be above the distal side of the insertion section 40, and the insertion section 40 is being subjected to right rotation. Even when a right-handed loop is formed in the insertion section 40 inserted along the insertion target 300, such control can assist loop releasing and straightening of the insertion section 40.

Therefore, the present embodiment can provide the endoscope apparatus 10 with improved insertability to the deep section and improved operability of the insertion section 40 in which the variable stiffness controller 10 controls the bending stiffness of the variable stiffness section 50 according to the various loop states such as the N-loop or the α-loop the insertion section 40 may form, so as to assist the loop releasing and straightening operation of the insertion section 40 of the endoscope 20.

In addition, after the variable stiffness controller 110 controls the variable stiffness drive section 70 so that the bending stiffness of the insertion section 40 is increased during the loop releasing and straightening operations, the variable stiffness controller 110 controls the variable stiffness drive section 70 so that the bending stiffness of the insertion section 40 is increased in response to determining that the loop of the insertion section 40 is released. As a result, the insertion section 40 can be inserted without applying a load to the intestine tract 301 by virtue of having high bending stiffness, when the insertion section 40 is pushed again toward the bent section.

In the case where the variable stiffness section 50 includes variable stiffness units, the variable stiffness controller 110 may drive a variable stiffness drive section 70 so that the bending stiffness of only a corresponding variable stiffness unit disposed that is disposed at a position where the loop of the insertion section 40 is formed is increased, in response to determining that the insertion section 40 forms a loop and that the operator has performed the rotation operation of the insertion section 40. Such control can promote the loop releasing and straightening operations, so that the insertability of the insertion section 40 into the deep section is improved.

Although the embodiments of the present invention have been described above, the present invention is not limited to the above-described embodiments, and various improvements and modifications can be made without departing from the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   a flexible tube section that is adapted to be inserted into an insertion target;
   a variable stiffness material that is disposed in the flexible tube section and configured to change a bending stiffness of the flexible tube section;
   a drive actuator configured to drive the variable stiffness material;
   a rotation detection sensor configured to detect rotation of the flexible tube section about a central axis;
   an insertion shape detection sensor configured to detect a curved shape of the flexible tube section; and
   a controller configured to control the drive actuator so that a bending stiffness of the variable stiffness material is increased in response to determining that the flexible tube section forms a loop and that the flexible tube section rotates about the central axis, based on rotation information detected by the rotation detection sensor and curved shape information detected by the insertion shape detection sensor;
   wherein the controller is configured to, based on the rotation information and the curved shape information,
   control the drive actuator so that the bending stiffness of the variable stiffness material is reduced in response to determining that the flexible tube section is being pushed, and
   control the drive actuator so that the bending stiffness of the variable stiffness material is increased in response to determining that the flexible tube section is being pulled out based on the rotation information and the curved shape information.

2. The flexible tube insertion apparatus according to claim 1, wherein the rotation detection sensor is a detection section that is attached to the flexible tube section and configured to detect at least one of a twist, a rotational torque, and a rotational distortion of the flexible tube section.

3. The flexible tube insertion apparatus according to claim 1, wherein the controller is configured to control the drive actuator so that the bending stiffness of the variable stiffness material is increased in response to determining that the flexible tube section forms the loop with a first crossover, the loop is left-handed from a proximal end side to a distal end side of the flexible tube section, the proximal end side of the flexible tube section crosses the distal end side of the flexible tube section so as to be below the distal end side of the flexible tube section, and the flexible tube section is being subjected to right rotation, or in response to determining that the flexible tube forms the loop with a second crossover, the loop is left-handed from the proximal end side to the distal end side of the flexible tube section, the proximal end side of the flexible tube section crosses the distal end side of the flexible tube section so as to be above the distal end side of the flexible tube section, and the flexible tube section is being subjected to left rotation, based on the rotation information and the curved shape information.

4. A flexible tube insertion method comprising:
   detecting rotation information of a flexible tube section about a central axis, the flexible tube section being adapted to be inserted into an insertion target;
   detecting curved shape information of the flexible tube section;
   controlling a variable stiffness material that is disposed in the flexible tube section and configured to change a bending stiffness of the flexible tube section so that a bending stiffness of the variable stiffness material is increased in response to determining that the flexible tube section forms a loop and the flexible tube section has been rotated about its central axis, based on the detected rotation information and the detected curved shape information;
   controlling a drive actuator so that the bending stiffness of the variable stiffness material is decreased in response to determining that a pushing operation is performed on the flexible tube section based on the rotation information and the curved shape information; and
   controlling the drive actuator so that the bending stiffness of the variable stiffness material is increased in response to determining that a pull-out operation is performed on the flexible tube section based on the rotation information and the curved shape information.

5. The flexible tube insertion method according to claim 4, wherein the detecting the rotation information includes detecting at least one of a twist, a rotational torque, and a rotational distortion of the flexible tube section by a rotation detection sensor attached to the flexible tube section.

6. The flexible tube insertion method according to claim 4, wherein the controlling the variable stiffness material includes controlling the drive actuator so that the bending stiffness of the variable stiffness material is increased in response to determining that the flexible tube section forms the loop with a first crossover, the loop is left-handed from a proximal end side to a distal end side of the flexible tube section, the proximal end side of the flexible tube section crosses the distal end side of the flexible tube section so as to be below the distal end side of the flexible tube section, and the flexible tube section is being subjected to right rotation; or in response to determining that the flexible tube forms the loop with a second crossover, the loop is left-handed from the proximal end side to the distal end side of the flexible tube section, the proximal end side of the flexible tube section crosses the distal end side of the flexible tube section so as to be above the distal end side of the flexible tube section, and the flexible tube section is being subjected to left rotation, based on the rotation information and the curved shape information.

* * * * *